United States Patent [19]

Heilman et al.

[11] 4,405,619

[45] Sep. 20, 1983

[54] ANTIINFLAMMATORY SUBSTITUTED-1,2,4-TRIAZOLO[4,3-b]-1,2,4-TRIAZINES

[75] Inventors: William P. Heilman, Chagrin Falls; James M. Gullo, Perry, both of Ohio

[73] Assignee: Diamond Shamrock Corporation, Dallas, Tex.

[21] Appl. No.: 298,789

[22] Filed: Sep. 2, 1981

[51] Int. Cl.$^3$ .................... C07D 487/04; A61K 31/41
[52] U.S. Cl. ..................................... 424/249; 544/184
[58] Field of Search .................... 544/184; 424/249

[56] References Cited

U.S. PATENT DOCUMENTS

| | | | |
|---|---|---|---|
| 3,333,961 | 8/1967 | Fry et al. | 544/184 |
| 3,398,148 | 8/1968 | Fry et al. | 544/184 |
| 4,159,375 | 6/1979 | Trust et al. | 544/184 |
| 4,260,756 | 4/1981 | Moran et al. | 544/236 |

FOREIGN PATENT DOCUMENTS 642615 5/1964 Belgium .

OTHER PUBLICATIONS

Fusco et al., *Rend. ist lombardo sci. Pt. I Classe Sci. mat. e nat.*, 88, 173(1955).
Hoggarth, *J. Chem. Soc.*, 612(1950).
*Ibid.*, 1579(1950).
*Ibid.*, 4817(1952).
Taylor, *J.A.C.S.*, 76, 619(1954).

*Primary Examiner*—John M. Ford
*Attorney, Agent, or Firm*—Walter C. Danison, Jr.

[57] ABSTRACT

Substituted 1,2,4-triazolo[4,3-b]-1,2,4-triazines have been found to be effective antiinflammatory and analgesic agents for warm-blooded animals. Pharmacological compositions thereof and methods of using same are described.

19 Claims, No Drawings

ANTIINFLAMMATORY SUBSTITUTED-1,2,4-TRIAZOLO[4,3-b]-1,2,4-TRIAZINES

BACKGROUND OF THE INVENTION

(1) Field of the Invention

This invention relates generally to various novel substituted-1,2,4-triazolo[4,3-b]-1,2,4-triazines which exhibit antiinflammatory and analgesic activity in warm-blooded animals. This invention also relates to pharmacological compositions and formulations containing these compounds and their use as antiinflammatory and analgesic agents.

(2) State of the Art

There are a number of compounds known today which exhibit antiinflammatory activity, many of which, however, exhibit undesirable side effects, e.g., neurotoxic side effects.

Substituted-triazolotriazine compounds having various substituents thereon have heretofore been prepared and proposed for use in a wide range of different ultimate applications, however, none of these applications involve use as antiinflammatory or analgesic agents.

For example, U.S. Pat. No. 4,159,379 discloses 6- and 7-aryl-1,2,4-triazolo[4,3,b]-1,2,4-triazines useful as an anxiolytic agents. A related class of compounds, i.e., 6- and 8-heteroaryl-1,2,4-triazolo[4,3-B]pyridazines, also useful for treating anxiety are disclosed in U.S. Pat. No. 4,260,756. A series of substituted-1,2,4-triazolo[4,3-b]-1,2,4-triazine compounds, including the 7-phenyl and the 3-methyl-7-phenyl derivatives, disclosed as being useful antitubercular agents, are described by R. Fusco et al., *Rend.ist lombardo sci. Pt. I Classe Sci. mat. e nat.*, 88, 173 (1955).

Belgium Pat. No. 642,615 (1964) discloses a series of substituted and unsubstituted 7-hydroxy-1,2,4-triazolo[4,3-b]-1,2,4-triazines useful as photographic emulsion stabilizers.

Various other similar series of triazolotriazine compounds have also been disclosed in the art, for example Hoggarth, *J. Chem. Soc.*, 612 (1950); *Ibid.*, 1579 (1950); *Ibid.*, 4817 (1952); Dornow et al., *Ber.*, 97 (8) 2179–84 (1964); and Taylor, *J.A.C.S.*, 76, 619 (1954). No indication is found in any of these references nor any of the above aforementioned references that the various respective triazolotriazine compounds exhibit antiinflammatory or analgesic activity or even any other related pharmacological activity.

SUMMARY OF THE INVENTION

It has now been discovered in accordance with the present invention novel substituted-1,2,4-triazolo[4,3-b]-1,2,4-triazine compounds of the following general formula:

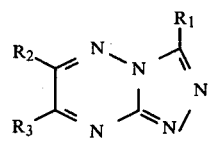

Further in accordance with the invention, active 1,2,4-triazolo[4,3-b]-1,2,4-triazine compounds are formulated into novel antiinflammatory and analgesic pharmaceutical preparations.

Still further in accordance with the present invention, a method for inducing or obtaining analgesic and antiinflammatory effects in mammals by the administration of preselected dosages of active substituted-1,2,4-triazolo[4,3-b]-1,2,4-triazine compounds in suitable nontoxic pharmaceutical dosage unit forms or compositions is provided.

These and other aspects and advantages of the invention will be appreciated by those skilled in the art from the specification and claims which follow.

DESCRIPTION OF THE PREFERRED EMBODIMENTS

A novel class of compounds has now been discovered which compounds are found to demonstrate antiinflammatory and/or analgetic activity having little or no neurotoxic side effects. The compounds which are the active ingredients of the present invention fit the general formula I below:

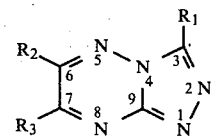

or a pharmaceutically acceptable nontoxic salt thereof wherein $R_1$ is hydrogen, alkyl, hydroxy, alkoxy, alkoxyalkyl, haloalkyl, cycloalkyl, phenyl, halophenyl, alkylphenyl or alkoxyphenyl; $R_2$ is hydrogen, alkyl, phenyl or pyridyl; and $R_3$ is alkyl, haloalkyl, aryl, haloaryl, alkylaryl, alkoxyaryl, hydroxyaryl or pyridyl.

As used throughout the instant specification and claims, the expressions "alkyl" and "alkoxy" are inclusive of straight and branch chain carbon-carbon linkages, e.g., methyl, ethyl, N-propyl, isopropyl, N-butyl, isobutyl, etc., and represent 1 to 5 carbon atoms, unless otherwise specified. The expression "pharmaceutically acceptable nontoxic salts" as used herein is intended to include those salts capable of being formed with the disclosed compounds and substituted derivatives thereof in accordance with the invention without materially altering the chemical structure or pharmacological properties of the parent compounds.

The 3,6,7-substituted triazolotriazine compounds of the present invention may be prepared by various alternative methods heretofore employed in the synthesis of other triazolo triazine compounds. Some of these methods are illustrated in the previously mentioned Belgium Pat. No. 642,615 and the literature reference to Fusco et al. For the purposes of this invention, the following general method was employed. An appropriately substituted ketone starting material was reacted with selenium dioxide to which the resulting reaction product was subsequently reacted with methylthiosemicarbazide. The resulting methylthio-1,2,4-triazine product was caused to be reacted with hydrazine to form a 3-hydrazino-1,2,4-triazine product, and this product was finally reacted with the appropriate carboxylic acid to give the desired 1,2,4-triazolo[4,3-b]-1,2,4-triazine. The foregoing general reaction scheme may be depicted as follows:

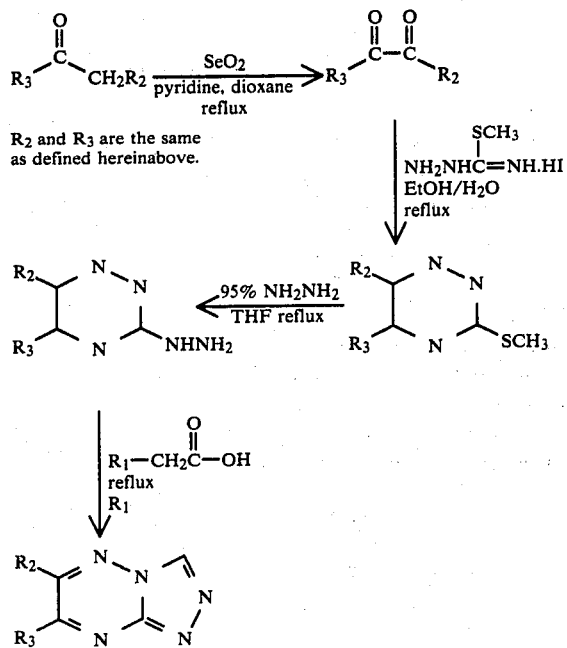

$R_2$ and $R_3$ are the same as defined hereinabove.

$R_1$ is the same as defined hereinabove.

As previously indicated, the compounds of the present invention evidence antiinflammatory and analgetic effects in warm-blooded animals. Of course, it will be appreciated that the specific response elicited upon administration of the compounds of the present invention to an animal species in need thereof will vary depending upon the specific structure of the administered compound, the unit dosage, dosage regimen and mode of administration, as well as the mammalian species involved.

Exemplary of preferred compounds for use in the antiinflammatory compositions and methods of the present invention are compounds of the above general formula I wherein, correspondingly, $R_1$ represents hydrogen, alkyl, hydroxy or alkoxyalkyl; $R_2$ represents hydrogen, alkyl or phenyl; and $R_3$ represents alkyl, phenyl, halophenyl or alkylphenyl.

As especially preferred compounds falling within the aforesaid general formula I are 1,2,4-triazolo[4,3-b]-1,2,4-triazine, 3-methyl-7-(3'-chlorophenyl); 1,2,4-triazolo[4,3-b]-1,2,4-triazine, 3-methyl-7-(3',4'-dichlorophenyl); 1,2,4-triazolo[4,3-b]-1,2,4-triazine, 3-methoxymethyl-7-phenyl; 1,2,4-triazolo[4,3-b]-1,2,4-triazine, 3-hydroxy-7-phenyl; 1,2,4-triazolo[4,3-b]-1,2,4-triazine, 7-(4'-chlorophenyl); 1,2,4-triazolo[4,3-b]-1,2,4-triazine, 3-isopropyl-7-phenyl; 1,2,4-triazolo[4,3-b]-1,2,4-triazine, 3-ethyl-7-phenyl; 1,2,4-triazolo[4,3-b]-1,2,4-triazine, 3-methyl-7-phenyl; 1,2,4-triazolo[4,3-b]-1,2,4-triazine, 7-phenyl; 1,2,4-triazolo[4,3-b]-1,2,4-triazine, 3-isopropyl-7-(3',4'-dichlorophenyl); 1,2,4-triazolo[4,3-b]-1,2,4-triazine, 7-(3',4'-dichlorophenyl); 1,2,4-triazolo[4,3-b]-1,2,4-triazine, 7-(4'-methylphenyl); 1,2,4-triazolo[4,3-b]-1,2,4-triazine, 6,7-diphenyl; 1,2,4-triazolo[4,3-b]-1,2,4-triazine, 3-methyl-6,7-diphenyl; 1,2,4-triazolo[4,3-b]-1,2,4-triazine, 3-isopropyl-6,7-diphenyl; 1,2,4-triazolo[4,3-b]-1,2,4-triazine, 3,6,7-trimethyl; 1,2,4-triazolo[4,3-b]-1,2,4-triazine, 3-methyl-7-(2'-chlorophenyl); and 1,2,4-triazolo[4,3-b]-1,2,4-triazine, 7-(2'-chlorophenyl). Most preferred compounds are 1,2,4-triazolo[4,3-b]-1,2,4-triazine, 3-methyl-7-(3'-chlorophenyl); 1,2,4-triazolo[4,3-b]-1,2,4-triazine, 3-hydroxy-7-phenyl; 1,2,4-triazolo[4,3-b]-1,2,4-triazine, 7-(4'-chlorophenyl); 1,2,4-triazolo[4,3-b]-1,2,4-triazine, 3-methyl-7-phenyl; and 1,2,4-triazolo[4,3-b]-1,2,4-triazine, 7-phenyl.

In accordance with the practice of the present invention, the active compounds of the invention may be administered alone or in combination with each other or administered in admixture with pharmaceutical diluents, carriers, excipients or adjuvants suitably selected with respect to the intended route of administration and conventional pharmaceutical practices. For instance, for oral administration in the form of tablets or capsules, the active compound or compounds of the invention may be combined with such excipients as starch, lactose, sucrose, cellulose, magnesium stearate, and the like. Similarly, injectable dosage unit forms may be utilized to accomplish intravenous, intramuscular or subcutaneous administration and, for such parenteral administration, suitable sterile aqueous or nonaqueous solutions or suspensions, optionally containing appropriate solutes to effectuate isotonicity, will be employed. Other suitable adjuvants and dosage forms will be apparent to those skilled in the art.

Compounds of the invention or compositions thereof may be administered to warm-blooded animals, i.e., mammals, including, for instance, mice, rats, guinea pigs, dogs and other domesticated animals, or humans. Dosages sufficient to elicit the above-identified antiinflammatory/analgesic response will generally range between about 1 to 500 mg/kg/day in laboratory mice based upon body weight, and preferably between about 50 to 300 mg/kg/day. The foregoing dosages will normally be administered in 3 or 4 divided doses, depending upon the desired dosage regimen. Of course, the actual effective dose to be administered will vary, depending upon the specific compounds involved, as well as the age, weight and responsiveness of the particular animal species.

The compounds of the invention exhibit relatively low toxicities and the acute oral $LD_{50}$ (lethal dose to 50 percent of mice) will generally be greater than 300 mg/kg and, with respect to certain compounds, up to as high as 600 mg/kg. Moreover, the compounds of the invention exhibit essentially no neurotoxic side effects at normal dosage levels. In general, compounds of the invention demonstrate $NTD_{50}$ values (the dose that causes minimal recognizable neurotoxicity to 50% of mice) in the range of 300 mg/kg to 1000 mg/kg and several compounds have $NTD_{50}$ values greater than 100 mg/kg.

Various features and aspects of the present invention will be further illustrated in the examples that follow. While these examples are presented to show one skilled in the art how to operate within the scope of this invention, they are not to serve as a limitation on the scope of the invention where such scope is only defined in the claims.

EXAMPLE 1

Preparation of Intermediate A 5-(3'-chlorophenyl)-3-methylthio-1,2,4-triazine

Into a 500 mL. flask equipped with a mechanical stirrer, heating mantle, thermometer and condenser were placed 34.4 g. (0.31 m.) of selenium dioxide, 250 mL. of dioxane and 10 mL. of water. The contents were heated to 60° C. and 46.4 g. (0.3 m.) of 3'-chloroacetophenone was added in one portion. The contents were heated at reflux for 2 hours, cooled and filtered. The solvents were removed under vacuum. The resulting 2-(3'-chlorophenyl)glyoxal was dissolved in 100 mL. of ethanol and additional selenium was filtered off.

Into a 500 mL. flask equipped with a magnetic stirrer, heating mantle and condenser were placed the above 50.6 g. (0.3 m.) of crude 2-(3'-chlorophenyl)glyoxal in 100 mL. of ethanol, 70 g. (0.3 m.) of S-methylthiosemicarbazide hydrogen iodide in 100 mL. of ethanol and 24 g. (0.3 m.) of pyridine. The contents were heated at reflux for one hour and cooled. The precipitated material was filtered off and extracted with 1200 mL. of hexane. The hexane was evaporated and the resulting material was crystallized from 200 mL. of methanol. There was obtained 26.0 g. (36.5% yield) of material melting at 79°-81° C.

Preparation of Intermediate B 3-hydrazino-5-(3'-chlorophenyl)-1,2,4-triazine

To a solution of 90 g. (0.38 m.) of 3-methylthio-5-(3'-chlorophenyl)-1,2,4-triazine was added 500 mL. of THF and 150 mL. of methanol. Then 70 mL. of 95% hydrazine was added and the solution was allowed to heat at reflux overnight. The cooled solution was poured into ice water. The resulting orange precipitate was filtered and dried. Following a recrystallization from methanol, 60 g. of the title compound was obtained, M.P. of 163°-166° C.

Preparation of Final Product 1,2,4-triazolo[4,3-b]-1,2,4-triazine, 3-methyl-7-(3-chlorophenyl)

In a 250 mL. round bottom flask was placed 3-hydrazino-5-(3-chlorophenyl)-1,2,4-triazine (INTERMEDIATE B—10 g., 0.03 m.) dissolved in an excess of glacial acetic acid. The mixture was refluxed for 24 hrs., cooled to form a yellow solid which was collected, dried under reduced pressure and sublimed at 235° C./0.1 mmHg to form a yellow powder, M.P. of 209°-210° C.

Note: For the following examples, the procedures for preparing the necessary intermediates are the same as set out in Example 1 the only difference being, of course, the appropriate starting material, M.P. of 209°-210° C.

EXAMPLE 2

1,2,4-triazolo[4,3-b]-1,2,4-triazine, 3-methoxymethyl-7-phenyl

To 20 g. (0.11 m.) of 3-hydrazino-5-phenyl-1,2,4-triazine was added 50 mL. of methoxyacetic acid. The solution was heated at reflux overnight. The reaction solution was poured into ice water and the resulting precipitate was filtered, washed with water and dried. Following a recrystallization from methanol, 16.3 g. of the title compound was obtained, M.P. of 171°-173° C.

EXAMPLE 3

1,2,4-triazolo[4,3-b]-1,2,4-triazine, 3-hydroxy-7-phenyl 50 g. (0.27 m.) of 3-hydrazino-5-phenyl-1,2,4-triazine was partially dissolved in 1.5 L. of 1,4-dioxane. Phosgene was then bubbled through the stirred mixture until the temperature reached 40° C. The gas flow was stopped and the mixture was heated at reflux for 1 hr. The mixture was cooled and the precipitate was filtered and dried. 10 g. of the precipitate recrystallized from DMF to yield 7.5 g. of the title compound, M.P. is greater than 280° C.

EXAMPLE 4

1,2,4-triazolo[4,3-b]-1,2,4-triazine, 3-isopropyl-7-phenyl

In a 500 mL. round bottom flask equipped with condenser and heating mantle was placed 3-hydrazino-5-phenyl-1,2,4-triazine (18.7 g., 0.1 m.) dissolved in warm isobutyric acid (100 mL.) and refluxed for 10 hrs. Upon cooling, the mixture was poured over ice to form a yellow solid which was recrystallized from isopropanol to give a yellow crystalline solid, M.P. of 154°-156° C.

EXAMPLE 5

1,2,4-triazolo[4,3-b]-1,2,4-triazine, 3-ethyl-7-phenyl

In a 500 mL. round bottom flask equipped with condenser was placed 3-hydrazino-5-phenyl-1,2,4-triazine (18.7 g., 0.1 m.) dissolved in excess propionic acid (100 mL.) and refluxed for 10 hrs. Upon cooling, the mixture was poured over ice, the solid formed, collected by filtration and recrystallized from warm DMF to afford yellow-green crystals, M.P. of 194°-196° C.

EXAMPLE 6

1,2,4-triazolo[4,3-b]-1,2,4-triazine, 3-isopropyl-7-(3',4'-dichlorophenyl)

In a 250 mL. round bottom flask was placed 3-hydrazino-5-(3',4'-dichlorophenyl)-1,2,4-triazine (10 g., 0.04 m.) dissolved in warm isobutyric acid (100 mL.). The mixture was refluxed for 10 hrs., cooled, diluted with $H_2O$ to form a yellow solid. The solid was collected, recrystallized from ethyl acetate/acetic acid to afford a yellow powder, M.P. of 217°-218° C.

EXAMPLE 7

1,2,4-triazolo[4,3-b]-1,2,4-triazine, 7-(3',4'-dichlorophenyl)

In a 250 mL. round bottom flask equipped with condenser and heating mantle was placed 3-hydrazino-5-(3',4'-dichlorophenyl)-1,2,4-triazine (10 g., 0.04 m.) dissolved in warm 88% formic acid (150 mL.). The mixture was refluxed for 10 hrs., cooled, diluted with $H_2O$ to afford an orange solid. The solid was collected, recrystallized from hot formic acid to give light orange plates, M.P. is greater than 260° C.

EXAMPLE 8

1,2,4-triazolo[4,3-b]-1,2,4-triazine, 3-methoxymethyl-7-(4'-methylphenyl)

In a 250 mL. round bottom flask equipped with condenser and heating mantle was placed 3-hydrazino-5-(3'-methylphenyl)-1,2,4-triazine (10 g., 0.05 m.) dissolved in excess methoxyacetic acid (150 mL.). The mixture was refluxed for 3 hrs. forming a yellow precipitate which increased upon addition of water and cooling. The solid was collected and recrystallized from acetic acid affording yellow crystals, M.P. of 174°-175° C.

EXAMPLE 9

1,2,4-triazolo[4,3-b]-1,2,4-triazine, 3-methyl-6,7-diphenyl

In a 500 mL. round bottom flask was placed 3-hydrazino-5,6-diphenyl-1,2,4-triazine (15 g., 0.05 m.) dissolved in excess glacial acetic acid (300 mL.). The mixture was refluxed for 10 hrs., cooled and diluted with water to form a tan solid. Recrystallization from isopropanol afforded a light tan powder, M.P. of 205°–207° C.

EXAMPLE 10

1,2,4-triazolo[4,3-b]-1,2,4-triazine, 7-(4'-chlorophenyl)

In a 250 mL. round bottom flask equipped with heating mantle and condenser was placed 3-hydrazino-5-(4'-chlorophenyl)-1,2,4-triazine (11 g., 0.05 m.) dissolved in excess formic acid (150 mL. of 88%). The mixture was refluxed for 12 hrs., cooled, the orange precipitate formed was collected, washed with $H_2O$ and acetone and recrystallized from hot formic acid to afford yellow-orange plates, M.P. is greater than 260° C.

EXAMPLE 11

1,2,4-triazolo[4,3-b]-1,2,4-triazine, 3-methyl-7-(4'-chlorophenyl)

In a 250 mL. round bottom flask equipped with condenser and heating mantle was placed 3-hydrazino-5-(4'-chlorophenyl)-1,2,4-triazine (11 g., 0.05 m.) dissolved in hot acetic acid (150 mL.). The mixture was refluxed for 13 hrs., cooled and diluted with 25 mL. of water. The precipitate which formed was collected, washed with water and acetone and recrystallized from acetic acid. Drying under reduced pressure afforded yellow powder, M.P. is greater than 260° C.

EXAMPLE 12

1,2,4-triazolo[4,3-b]-1,2,4-triazine, 3-methyl-7-phenyl

In a 250 mL. flask equipped with a magnetic stirrer, heating mantle and condenser were placed 7.5 g. (0.04 m.) of 3-hydrazino-5-phenyl-1,2,4-triazine and 100 mL. of acetic acid. The contents were heated at reflux for 8 hrs. and the excess acetic acid was evaporated off under vacuum. The resulting material was neutralized with aqueous sodium bicarbonate and then crystallized from 400 mL. of methanol. There was obtained 4.5 g. (53.5% yield) of material, melting at 231°–232° C.

The following compounds were prepared utilizing synthesis methods analogous to the foregoing.

EXAMPLE 13

1,2,4-triazolo[4,3-b]-1,2,4-triazine, 7-phenyl

Melting point 253°–254° C.

EXAMPLE 14

1,2,4-triazolo[4,3-b]-1,2,4-triazine, 3-cyclopentyl-7-phenyl

Melting point 192°–194° C.

EXAMPLE 15

1,2,4-triazolo[4,3-b]-1,2,4-triazine, 3-trifluoromethyl-7-phenyl

Melting point 196°–198° C.

EXAMPLE 16

1,2,4-triazolo[4,3-b]-1,2,4-triazine, 3-butyl-7-phenyl

Melting point 151°–153° C.

EXAMPLE 17

1,2,4-triazolo[4,3-b]-1,2,4-triazine, 7-(4'-methylphenyl)

Melting point 280° C.

EXAMPLE 18

1,2,4-triazolo[4,3-b]-1,2,4-triazine, 3-isopropyl-7-(4'-methylphenyl)

Melting point 170°–172° C.

EXAMPLE 19

1,2,4-triazolo[4,3-b]-1,2,4-triazine, 7-(4'-hydroxyphenyl)-3-methyl

Melting point 211°–213° C.

EXAMPLE 20

1,2,4-triazolo[4,3-b]-1,2,4-triazine, 3-isopropyl-7-(4'-methoxyphenyl)

Melting point 205°–207° C.

EXAMPLE 21

1,2,4-triazolo[4,3-b]-1,2,4-triazine, 7-(4'-methoxyphenyl)

Melting point 274°–275° C.

EXAMPLE 22

1,2,4-triazolo[4,3-b]-1,2,4-triazine, 6,7-diphenyl

Melting point 180°–182° C.

EXAMPLE 23

1,2,4-triazolo[4,3-b]-1,2,4-triazine, 3-isopropyl-5,6-diphenyl

Melting point 148°–151° C.

EXAMPLE 24

1,2,4-triazolo[4,3-b]-1,2,4-triazine, 3-methyl-7-(4'-methoxyphenyl)

Melting point 242°–243° C.

EXAMPLE 25

1,2,4-triazolo[4,3-b]-1,2,4-triazine, 3,6,7-trimethyl

Melting point 166°–168° C.

EXAMPLE 26

1,2,4-triazolo[4,3-b]-1,2,4-triazine, 3-methyl-7-(2'-chlorophenyl)

Melting point 185°–187° C.

EXAMPLE 27

1,2,4-triazolo[4,3-b]-1,2,4-triazine, 7-(2',5'-dichlorophenyl)

Melting point is greater than 280° C.

EXAMPLE 28

1,2,4-triazolo[4,3-b]-1,2,4-triazine, 7-(3'-chlorophenyl)

Melting point is greater than 280° C.

EXAMPLE 29

1,2,4-triazolo[4,3-b]-1,2,4-triazine, 3-methyl-6,7-bis(2'-pyridyl)

Melting point 220°–223° C.

EXAMPLE 30

1,2,4-triazolo[4,3-b]-1,2,4-triazine, 3-methyl-7-(4'-hydroxyphenyl)

Melting point is greater than 270° C.

EXAMPLE 31

1,2,4-triazolo[4,3-b]-1,2,4-triazine, 3-methyl-6,7-bis(4'-chlorophenyl)

Melting point 235°–237° C.

EXAMPLE 32

1,2,4-triazolo[4,3-b]-1,2,4-triazine, 3-methyl-7-tertbutyl

Melting point 243°–245° C.

EXAMPLE 33

1,2,4-triazolo[4,3-b]-1,2,4-triazine, 3-methyl-7-(4'-methylphenyl)

Melting point 213°–216° C.

EXAMPLE 34

1,2,4-triazolo[4,3-b]-1,2,4-triazine, 3-methyl-7-(2',5'-dichlorophenyl)

Melting point 275°–277° C.

EXAMPLE 35

1,2,4-triazolo[4,3-b]-1,2,4-triazine, 3-methyl-7-(3',4'-dichlorophenyl)

Melting point 270°–273° C.

EXAMPLE 36

1,2,4-triazolo[4,3-b]-1,2,4-triazine, 7-(2'-chlorophenyl)

Melting point 162°–164° C.

PHARMACOLOGICAL ACTIVITY

The results of stuides demonstrating the indicated antiinflammatory and analgesic effects observed upon administration of effective dosages of typical preferred compounds in accordance with the present invention and the procedures utilized to evaluate pharmacological activity are set forth below.

A. Antiinflammatory Assay

Antiinflammtory activity, i.e., effectiveness in the prevention and inhibition of granuloma tissue formation, is demonstrated by relative inhibition of carrageenin-induced edema as determined by the diminution of experimental edema induced in the hind paw of a rat by the injection of carrageenin. The procedure employed is a modification of the method of Winter et al., *Proc. Soc. Exptl. Biol. Med.*, 111:544 (1962). The device used for measurement of the paw volume is an adaptation of the water displacement procedure described by Adamkiewicz et al., *Can. J. Biochem. Physiol.*, 33:332 (1955). Test compounds were administered orally, one hour prior to the intraplanter injection of 0.05 mL. of sterile 1.0% solution of carrageenin into the left hind paw of male rats (Long Evans strain) weighing between about 130–200 g. At peak swelling time (3 hrs.) the volume of edema was calculated by differential paw volumes.

Table I sets forth the results obtained at the indicated dosages for each of the identified compounds.

TABLE I

| | Carrageenin Assay | |
|---|---|---|
| Compd. Example No. | Dose (mg/kg) | % Reduction of Edema |
| 1 | 200 | 39 |
| 2 | 200 | 26 |
| 3 | 200 | 22 |
| 4 | 200 | 18 |
| 5 | 200 | 40 |
| 6 | 200 | 33 |
| 7 | 200 | 36 |
| 8 | 100 | 16 |
| 9 | 200 | 35 |
| 10 | 200 | 27 |
| 12 | 200 | 70 |
| 13 | 175 | 82 |
| 15 | 200 | 30 |
| 22 | 200 | 32 |
| 23 | 200 | 37 |
| 25 | 200 | 49 |
| 26 | 200 | 56 |
| 28 | 200 | 21 |
| 36 | 200 | 65 |

Selected compounds of the invention were further tested to determine their $ED_{50}$ values. The $ED_{50}$ value is defined as that dose which reduced edema formation by about 25% or more compared with the mean control response (parallel run) in 50% of the animals. Typical results of these tests appear in Table II.

TABLE II

| $ED_{50}$ vs. Carrageenin Assay | |
|---|---|
| Compd. Example No. | $ED_{50}$ (mg/kg) |
| 1 | 30 |
| 5 | 100 |
| 7 | 1.0 |
| 10 | 10 |
| 23 | 30 |

B. Analgesic Assay

Phenylquinone writhing test was employed to evaluate analgesic activity for selected compounds for the present invention according to the following procedure:

Phenylquinone (phenyl-p-benzoquinone, No. 7104, Eastman Organic Chemicals) is made up as a 0.02% aqueous solution and 5% ethyl alcohol. Phenylquinone solutions are made up fresh twice daily. Standard reference agents and the test compounds are dissolved or suspended in a 0.25% methylcellulose solution. A control group consisting of 10 mice (Carworth $CF_1$ male mice) are administered the 0.02% phenylquinone solution at a dose of 0.25 mL./mouse. The mice are housed individually and observed closely for 10 min. for exhibition of writhing. The onset of writhing occurs within 3 min. and 100% of the mice must writh within 10 min. Test compounds are administered orally to groups of 10 mice. The volume given is 0.01 mL. per gram of body weight. Activity can be studied at 15, 30, 60 and 120 min. after oral administration. After the designated time interval of a dose group has elapsed, the mice are challenged with phenylquinone intraperitoneally. Complete blocking of the writhing syndrome for the 10-min. observation period in any one mouse is considered a positive analgesic response for that mouse. Conversely, if any mouse wriths definitely once, it is considered not to be protected. The number of mice not writhing in a group multiplied by 10 equals percent analgesia for that dose at the time interval.

The compounds tested, dose administered, and analgesic response are summarized in Table III.

TABLE III

| Phenylquinone Writhing Assay (% Control) | | | | |
|---|---|---|---|---|
| Compd. Example No. | Dose (mg/kg) | 15 min. | 30 min. | 60 min. |
| 4 | 100 | 10 | 20 | 20 |
| 5 | 100 | 30 | 30 | 70 |
| 7 | 100 | 30 | 50 | 30 |
| 13 | 50 | 20 | 20 | — |

While the invention has been described and illustrated with reference to certain preferred embodiments thereof, those skilled in the art will appreciate that various changes, modifications and substitutions can be made therein without departing from the spirit of the invention. For example, effective dosages other than the preferred ranges set forth hereinabove may be applicable as a consequence of variations in the responsiveness of the animal treated, severity of observed conditions, i.e., inflammation, fever, pain, etc., dosage related adverse effects, if any, observed and analogous considerations. Likewise, the specific pharmacological responses observed may vary depending upon the particular active compounds selected or whether different active compounds are used in combination or in the presence of suitable pharmaceutical carriers as well as the type of formulation and mode of administration employed and such expected variations or differences in results are contemplated in accordance with the practice of the present invention. It is intended, therefore, that the invention be limited only by the scope of the claims which follow.

What is claimed is:

1. A compound of the formula:

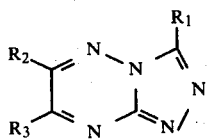

or a pharmaceutically acceptable nontoxic salt thereof wherein $R_1$ represents hydrogen, alkyl, haloalkyl, alkoxy, alkoxyalkyl, hydroxy, cycloalkyl, phenyl, halophenyl, alkylphenyl or alkoxyphenyl;

$R_2$ is hydrogen, alkyl, phenyl or pyridyl; and $R_3$ is alkyl, haloalkyl, aryl, haloaryl, alkylaryl, alkoxyaryl, hydroxyaryl or pyridyl;

subject to the provisos that when $R_3$ is alkyl, phenyl or halophenyl or alkoxyphenyl, $R_1$ is other than hydrogen, alkyl, phenyl or alkoxyphenyl and when $R_2$ and $R_3$ are both phenyl, $R_1$ is other than hydrogen or phenyl; wherein the terms alkyl and alkoxy as used herein are inclusive of straight and branch chain carbon-carbon linkages and represent 1 to 5 carbon atoms and the term aryl as used herein represents a carbocyclic ring of 6 to 10 carbon atoms.

2. The compound as defined in claim 1 wherein said compound is selected from the group consisting of 1,2,4-triazolo[4,3-b]-1,2,4-triazine, 3-methyl-7-(3'-chlorophenyl); 1,2,4-triazolo[4,3-b]-1,2,4-triazine, 3-methyl-7-(3',4'-dichlorophenyl); 1,2,4-triazolo[4,3-b]-1,2,4-triazine, 3-methoxymethyl-7-phenyl; 1,2,4-triazolo[4,3-b]-1,2,4-triazine, 3-hydroxy-7-phenyl; 1,2,4-triazolo[4,3-b]-1,2,4-triazine, 7-(4'-chlorophenyl); 1,2,4-triazolo[4,3-b]-1,2,4-triazine, 3-isopropyl-7-phenyl; 1,2,4-triazolo[4,3-b]-1,2,4-triazine, 3-ethyl-7-phenyl; 1,2,4-triazolo[4,3-b]-1,2,4-triazine, 3-methyl-7-phenyl; 1,2,4-triazolo[4,3b]-1,2,4-triazine, 7-phenyl; 1,2,4-triazolo[4,3-b]-1,2,4-triazine, 3-isopropyl-7-(3',4'-dichlorophenyl); 1,2,4-triazolo[4,3-b]-1,2,4-triazine, 7-(3',4'-dichlorophenyl); 1,2,4-triazolo[4,3-b]-1,2,4-triazine, 7-(4'-methylphenyl); 1,2,4-triazolo[4,3-b]-1,2,4-triazine, 6,7-diphenyl; 1,2,4-triazolo[4,3-b]-1,2,4-triazine, 3-methyl-6,7-diphenyl; 1,2,4-triazolo[4,3-b]-1,2,4-triazine, 3-isopropyl-6,7-diphenyl; 1,2,4-triazolo[4,3-b]-1,2,4-triazine, 3,6,7-trimethyl; 1,2,4-triazolo[4,3-b]-1,2,4-triazine, 3-methyl-7-(2'-chlorophenyl); and 1,2,4-triazolo[4,3-b]-1,2,4-triazine, 7-(2'-chlorophenyl).

3. The compound of claim 2 wherein said compounds are selected from the group consisting of 1,2,4-triazolo[4,3-b]-1,2,4-triazine, 3-methyl-7-(3'-chlorophenyl); 1,2,4-triazolo[4,3-b]-1,2,4-triazine, 3-hydroxy-7-phenyl; 1,2,4-triazolo[4,3-b]-1,2,4-triazine, 7-(4'-chlorophenyl); 1,2,4-triazolo[4,3-b]-1,2,4-triazine, 3-methyl-7-phenyl; and 1,2,4-triazolo[4,3-b]-1,2,4-triazine, 7-phenyl.

4. A pharmaceutical antiinflammatory preparation in dosage unit form comprised of a pharmaceutical carrier and an active ingredient, the active ingredient of which consists of a nontoxic antiinflammatory amount of a compound of the formula:

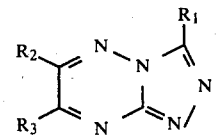

or a pharmaceutically acceptable nontoxic salt thereof wherein $R_1$ represents hydrogen, alkyl, haloalkyl, alkoxy, alkoxyalkyl, hydroxy, cycloalkyl, phenyl, halophenyl, alkylphenyl or alkoxyphenyl; $R_2$ is hydrogen, alkyl, phenyl or pyridyl; and $R_3$ is alkyl, haloalkyl, aryl, haloaryl, alkylaryl, alkoxyaryl, hydroxyaryl or pyridyl; wherein the terms alkyl and alkoxy as used herein are inclusive of straight and branch chain carbon-carbon linkages and represent 1 to 5 carbon atoms and the term aryl as used herein represents a carbocyclic ring of 6 to 10 carbon atoms.

5. A preparation as defined in claim 4 wherein said active ingredient is a compound or mixture of compound selected from the group consisting of 1,2,4-triazolo[4,3b]-1,2,4-triazine, 3-methyl-7-(3'-chlorophenyl); 1,2,4-triazolo[4,3-b]-1,2,4-triazine, 3-methyl-7-(3',4'-dichlorophenyl); 1,2,4-triazolo[4,3-b]-1,2,4-triazine, 3-methoxymethyl-7-phenyl; 1,2,4-triazolo[4,3-b]-1,2,4-triazne, 3-hydroxy-7-phenyl; 1,2,4-triazolo[4,3-b]-1,2,4-triazine, 7-(4'-chlorophenyl); 1,2,4-triazolo[4,3-b]-1,2,4-triazine, 3-isopropyl-7-phenyl; 1,2,4-triazolo[4,3-b]-1,2,4-triazine, 3-ethyl-7-phenyl; 1,2,4-triazolo[4,3-b]-1,2,4-triazine, 3-methyl-7-phenyl; 1,2,4-triazolo[4,3-b]-1,2,4-triazine, 7-phenyl; 1,2,4-triazolo[4,3-b]-1,2,4-triazine, 3-isopropyl-7-(3',4'-dichlorophenyl); 1,2,4-triazolo[4,3-b]-1,2,4triazine, 7-(3',4'-dichlorophenyl); 1,2,4-triazolo[4,3-b]-1,2,4-triazine, 7-(4'-methylphenyl); 1,2,4-triazolo[4,3-b]-1,2,4-triazine, 6,7-diphenyl; 1,2,4- triazolo[4,3-b]-1,2,4-triazine, 3-methyl-6,7-diphenyl; 1,2,4-triazolo[4,3-b]-1,2,4-triazine, 3-isopropyl-6,7-diphenyl; 1,2,4-triazolo[4,3-b]-1,2,4-triazine, 3,6,7-trimethyl; 1,2,4-triazolo[4,3-b]-1,2,4-triazine, 3-methyl-7-(2'-chlorophenyl); and 1,2,4-triazolo[4,3-b]-1,2,4-triazine, 7-(2'-chlorophenyl).

6. A preparation as defined in claim 4 wherein the active ingredient is a compound or mixture of compounds selected from the group consisting of 1,2,4-triazolo[4,3-b]-1,2,4-triazine, 3-methyl-7-(3'-chlorophenyl); 1,2,4-triazolo[4,3-b]-1,2,4-triazine, 3-hydroxy-7-phenyl; 1,2,4-triazolo[4,3-b]-1,2,4-triazine, 7-(4'-chlorophenyl); 1,2,4-triazolo[4,3-b]-1,2,4-triazine, 3-methyl-7-phenyl; and 1,2,4-triazolo[4,3-b]-1,2,4-triazine, 7-phenyl.

7. A preparation as defined in claim 4, 5 or 6 wherein the antiinflammatory amount is within the range of 50 to 500 mg/kg/day.

8. A method of obtaining an antiinflammatory effect in an animal in need thereof comprising administering thereto an antiinflammatory effective amount of a compound of the formula:

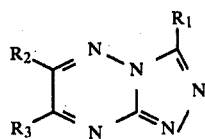

or a pharmaceutically acceptable nontoxic salt thereof wherein $R_1$ represents hydrogen, alkyl, haloalkyl, alkoxy, alkoxyalkyl, hydroxy, cycloalkyl, phenyl, halophenyl, alkylphenyl or alkoxyphenyl; $R_2$ is hydrogen, alkyl, phenyl or pyridyl; and $R_3$ is alkyl, haloalkyl, aryl, haloaryl, alkylaryl, alkoxyaryl, hydroxyaryl or pyridyl; wherein the terms alkyl and alkoxy as used herein are inclusive of straight and branch chain carbon-carbon linkages and represent 1 to 5 carbon atoms and the term aryl as used herein represents a carbocyclic ring of 6 to 10 carbon atoms.

9. The method of claim 8 wherein said compound is selected from the group consisting of 1,2,4-triazolo[4,3-b]-1,2,4-triazine, 3-methyl-7-(3'-chlorophenyl); 1,2,4-triazolo[4,3-b]-1,2,4-triazine, 3-methyl-7-(3',4'-dichlorophenyl); 1,2,4-triazolo[4,3-b]-1,2,4-triazine, 3-methoxymethyl-7-phenyl; 1,2,4-triazolo[4,3-b]-1,2,4-triazine, 3-hydroxy-7-phenyl; 1,2,4-triazolo[4,3-b]-1,2,4-triazine, 7-(4'-chlorophenyl); 1,2,4-triazolo[4,3-b]-1,2,4-triazine, 3-isopropyl-7-phenyl; 1,2,4-triazolo[4,3-b]-1,2,4-triazine, 3-ethyl-7-phenyl; 1,2,4-triazolo[4,3-b]-1,2,4-triazine, 3-methyl-7-phenyl; 1,2,4-triazolo[4,3-b]-1,2,4-triazine, 7-phenyl; 1,2,4-triazolo[4,3-b]-1,2,4-triazine, 3-isopropyl-7-(3',4'-dichlorophenyl); 1,2,4-triazolo[4,3-b]-1,2,4-triazine, 7-(3',4'-dichlorophenyl); 1,2,4-triazolo[4,3-b]-1,2,4-triazine, 7-(4'-methylphenyl); 1,2,4-triazolo[4,3-b]-1,2,4-triazine, 6,7-diphenyl; 1,2,4-triazolo[4,3-b]-1,2,4-triazine, 3-methyl-6,7-diphenyl; 1,2,4-triazolo[4,3-b]-1,2,4-triazine, 3-isopropyl-6,7-diphenyl; 1,2,4-triazolo[4,3-b]-1,2,4-triazine, 3,6,7-trimethyl; 1,2,4-triazolo[4,3-b]-1,2,4-triazine, 3-methyl-7-(2'-chlorophenyl); and 1,2,4-triazolo[4,3-b]-1,2,4-triazine, 7-(2'-chlorophenyl).

10. The method of claim 8 wherein said compound is selected from the group consisting of 1,2,4-triazolo[4,3-b]-1,2,4-triazine, 3-methyl-7-(3'-chlorophenyl); 1,2,4-triazolo[4,3-b]-1,2,4-triazine, 3-hydroxy-7-phenyl; 1,2,4-triazolo[4,3-b]-1,2,4-triazine, 7-(4'-chlorophenyl); 1,2,4-triazolo[4,3-b]-1,2,4-triazine, 3-methyl-7-phenyl; and 1,2,4-triazolo[4,3-b]-1,2,4-triazine, 7-phenyl.

11. The method of claim 8, 9 or 10 wherein the antiinflammatory amount is within the range of 50 to 500 mg/kg/day.

12. A pharmaceutical analgesic preparation in dosage unit form comprised of a pharmaceutical carrier and an active ingredient, the active ingredient of which consists of a nontoxic analgesic amount of a compound of the formula:

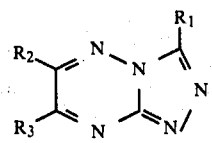

or a pharmaceutically acceptable nontoxic salt thereof wherein $R_1$ represents hydrogen, alkyl, haloalkyl, alkoxy, alkoxyalkyl, hydroxy, cycloalkyl, phenyl, halophenyl, alkylphenyl or alkoxyphenyl; $R_2$ is hydrogen, alkyl, phenyl or pyridyl; and $R_3$ is alkyl, haloalkyl, aryl, haloaryl, alkylaryl, alkoxyaryl, hydroxyaryl or pyridyl; wherein the terms alkyl and alkoxy as used herein are inclusive of straight and branch chain carbon-carbon linkages and represent 1 to 5 carbon atoms and the term aryl as used herein represents a carbocyclic ring of 6 to 10 carbon atoms.

13. A preparation as defined in claim 12 wherein the active ingredient is a compound or mixture of compounds selected from the group consisting of 1,2,4-triazolo[4,3-b]-1,2,4-triazine, 3-methyl-7-(3'-chlorophenyl); 1,2,4-triazolo[4,3-b]-1,2,4-triazine, 3-methyl-7-(3',4'-dichlorophenyl); 1,2,4-triazolo[4,3-b]-1,2,4-triazine, 3-methoxymethyl-7-phenyl; 1,2,4-triazolo[4,3-b]-1,2,4-triazine, 3-hydroxy-7-phenyl; 1,2,4-triazolo[4,3-b]-1,2,4-triazine, 7-(4'-chlorophenyl); 1,2,4-triazolo[4,3-b]-1,2,4-triazine, 3-isopropyl-7-phenyl; 1,2,4-triazolo[4,3-b]-1,2,4-triazine, 3-ethyl-7-phenyl; 1,2,4-triazolo[4,3-b]-1,2,4-triazine, 3-methyl-7-phenyl; 1,2,4-triazolo[4,3-b]-1,2,4-triazine, 7-phenyl; 1,2,4-triazolo[4,3-b]-1,2,4-triazine, 3-isopropyl-7-(3',4'-dichlorophenyl); 1,2,4-triazolo[4,3-b]-1,2,4-triazine, 7-(3',4'-dichlorophenyl); 1,2,4-triazolo[4,3-b]-1,2,4-triazine, 7-(4'-methylphenyl); 1,2,4-triazolo[4,3-b]-1,2,4-triazine, 6,7-diphenyl; 1,2,4-triazolo[4,3-b]-1,2,4-triazine, 3-methyl-6,7-diphenyl; 1,2,4-triazolo[4,3-b]-1,2,4-triazine, 3-isopropyl-6,7-diphenyl; 1,2,4-triazolo[4,3-b]-1,2,4-triazine, 3,6,7-trimethyl; 1,2,4-triazolo[4,3-b]-1,2,4-triazine, 3-methyl-7-(2'-chlorophenyl); and 1,2,4-triazolo[4,3-b]-1,2,4-triazine, 7-(2'-chlorophenyl).

14. A preparation as defined in claim 12 wherein the active ingredient is the compound 1,2,4-triazolo[4,3-b]-1,2,4-triazine, 3-ethyl-7-phenyl; 1,2,4-triazolo[4,3-b]-1,2,4-triazine, 7-(3',4'-dichlorophenyl); or a mixture thereof.

15. A preparation as defined in claim 12, 13 or 14 wherein the antiinflammatory amount is within the range of 50 to 500 mg/kg/day.

16. A method of obtaining an analgesic effect in an animal in need thereof comprising administering thereto an analgesic effective amount of an active ingredient containing a compound or mixture of compounds of the formula:

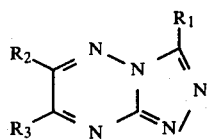

or a pharmaceutically acceptable nontoxic salt thereof wherein $R_1$ represents hydrogen, alkyl, haloalkyl, alkoxy, alkoxyalkyl, hydroxy, cycloalkyl, phenyl, halophenyl, alkylphenyl or alkoxyphenyl; $R_2$ is hydrogen, alkyl, phenyl or pyridyl; and $R_3$ is alkyl, haloalkyl, aryl, haloaryl, alkylaryl, alkoxyaryl, hydroxyaryl or pyridyl; wherein the terms alkyl and alkoxy as used herein are inclusive of straight and branch chain carbon-carbon linkages and represent 1 to 5 carbon atoms and the term aryl as used herein represents a carbocyclic ring of 6 to 10 carbon atoms.

17. The method of claim 16 wherein said active ingredient is a compound or mixture of compounds selected from the group consisting of 1,2,4-triazolo[4,3-b]-1,2,4-triazine, 3-methyl-7-(3'-chlorophenyl); 1,2,4-triazolo[4,3-b]-1,2,4-triazine, 3-methyl-7-(3',4'-dichlorophenyl); 1,2,4-triazolo[4,3-b]-1,2,4-triazine, 3-methoxymethyl-7-phenyl; 1,2,4-triazolo[4,3-b]-1,2,4-triazine, 3-hydroxy-7-phenyl; 1,2,4-triazolo[4,3-b]-1,2,4-triazine, 7-(4'-chlorophenyl); 1,2,4-triazolo[4,3-b]-1,2,4-triazine, 3-isopropyl-7-phenyl; 1,2,4-triazolo[4,3-b]-1,2,4-triazine, 3-ethyl-7-phenyl; 1,2,4-triazolo[4,3-b]-1,2,4-triazine, 3-methyl-7-phenyl; 1,2,4-triazolo[4,3-b]-1,2,4-triazine, 7-phenyl; 1,2,4-triazolo[4,3-b]-1,2,4-triazine, 3-isopropyl-7-(3',4'-dichlorophenyl); 1,2,4-triazolo[4,3-b]-1,2,4-triazine, 7-(3',4'-dichlorophenyl); 1,2,4-triazolo[4,3-b]-1,2,4-triazine, 7-(4'-methylphenyl); 1,2,4-triazolo[4,3-b]-1,2,4-triazine, 6,7-diphenyl; 1,2,4-triazolo[4,3-b]-1,2,4-triazine, 3-methyl-6,7-diphenyl; 1,2,4-triazolo-[4,3-b]-1,2,4-triazine, 3-isopropyl-6,7-diphenyl; 1,2,4-triazolo[4,3-b]-1,2,4-triazine, 3,6,7-trimethyl; 1,2,4-triazolo[4,3-b]-1,2,4-triazine, 3-methyl-7-(2'-chlorophenyl); and 1,2,4-triazolo[4,3-b]-1,2,4-triazine, 7-(2'-chlorophenyl).

18. The method of claim 16 wherein said active ingredient is a compound 1,2,4-triazolo[4,3-b]-1,2,4-triazine, 3-ethyl-7-phenyl; 1,2,4-triazolo[4,3-b]-1,2,4-triazine, 7-(3',4'-dichlorophenyl); or a mixture thereof.

19. A method as defined in claim 16, 17 or 18 wherein the antiinflammatory amount is within the range of 50 to 500 mg/kg/day.

* * * * *